United States Patent
Lee et al.

(10) Patent No.: US 6,627,383 B2
(45) Date of Patent: Sep. 30, 2003

(54) PHOTORESIST MONOMER COMPRISING BISPHENOL DERIVATIVES AND POLYMERS THEREOF

(75) Inventors: Geun Su Lee, Ichon-shi (KR); Jae Chang Jung, Ichon-shi (KE); Min Ho Jung, Ichon-shi (KR); Ki Ho Baik, Ichon-shi (KR)

(73) Assignee: Hynix Semiconductor Inc, Kyungki-Do (KR)

( * ) Notice: Subject to any disclaimer, the term of this patent is extended or adjusted under 35 U.S.C. 154(b) by 128 days.

(21) Appl. No.: 09/973,630

(22) Filed: Oct. 9, 2001

(65) Prior Publication Data

US 2002/0051940 A1 May 2, 2002

(30) Foreign Application Priority Data

Oct. 25, 2000 (KR) ........................................ 2000-62882

(51) Int. Cl.$^7$ ............................................... G03C 1/492
(52) U.S. Cl. .................... 430/270.1; 430/326; 430/907; 526/219.6; 526/232.1; 526/227; 526/242; 526/326; 526/328.5
(58) Field of Search .............................. 430/270.1, 326, 430/907; 526/242, 326, 328.5, 232.1, 227, 219.6

(56) References Cited

U.S. PATENT DOCUMENTS 5,380,901 A * 1/1995 Antonucci et al. .......... 556/440
6,511,787 B2 * 1/2003 Harada et al. ............ 430/270.1

FOREIGN PATENT DOCUMENTS

JP 04-366115 A * 12/1992

OTHER PUBLICATIONS

Derwent Abstract of JP 04–366115 A Dec. 1992.*

* cited by examiner

Primary Examiner—Rosemary Ashton
(74) Attorney, Agent, or Firm—Marshall, Gerstein & Borun

(57) ABSTRACT

Photoresist monomers of following Formula 1, photoresist polymers thereof, and photoresist compositions using the same. The photoresist composition has excellent etching resistance, heat resistance and adhesiveness, and is developable in aqueous tetramethylammonium hydroxide (TMAH) solution. In addition, the photoresist composition has low light absorbance at the wavelength of 193 nm, 157 nm and 13 nm, and thus is suitable for a photolithography process using ultraviolet light sources such as VUV (157 nm) and EUV (13 nm) in fabricating a minute circuit for a high integration semiconductor device.

Formula 1

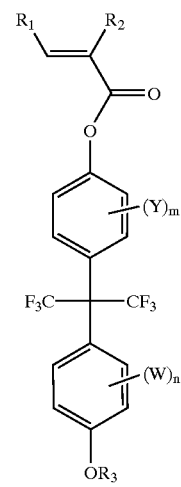

wherein, $R_1$, $R_2$, $R_3$, Y, W, m and n are as defined in the specification.

20 Claims, 6 Drawing Sheets

PHOTORESIST MONOMER COMPRISING BISPHENOL DERIVATIVES AND POLYMERS THEREOF

BACKGROUND

1. Technical Field

Novel photoresist monomers, polymers thereof, and photoresist compositions using the same are disclosed. In particular, photoresist polymers suitable for a photolithography process using DUV (deep ultraviolet) light sources such as VUV (157 nm) and EUV (13 nm) in fabricating a minute circuit for a high integration semiconductor device, photoresist compositions using the same, and preparation processes therefor are disclosed.

2. Description of the Background Art

In general, a useful photoresist for ArF and VUV has a variety of desired characteristics, such as low light absorbance at the wavelength of 193 nm and 157 nm, excellent etching resistance, and excellent adhesiveness to a wafer. In addition, a photoresist should be easily developable in a commercially readily available developing solution, such as 2.38 wt % and 2.6 wt % aqueous tetramethylammonium hydroxide (TMAH) solution.

Recently, there has been much research done on resins having a high transparency at the wavelength of 193 nm and dry etching resistance similar to novolac resin. However, most of the photoresists are not suitable for VUV due to their poor transmittance at 157 nm wavelength.

Photoresists containing fluorine and silicon have good transmittance at these wavelengths. Unfortunately, most photoresists containing fluorine with a polyethylene or polyacrylate polymer backbone have weak etching resistance, low solubility in an aqueous TMAH solution and poor adhesiveness to the silicon wafer. Furthermore, solubility of the resin is remarkably improved by introducing strong acid alcohol groups (pKa $\leq 12$), but the resin still remains unsatisfactory as a photoresist. It results from a low glass transition temperature (Tg) of the resin, a low contrast ratio between exposed and unexposed regions, and low adhesiveness to the wafer. On the other hand, photoresists containing silicon require a 2-step etching process of HF treatment and $O_2$ treatment. And it is difficult to remove HF completely, which makes these types of photoresists unsuitable to be applied into production.

SUMMARY OF THE DISCLOSURE

In an attempt to overcome the above-described disadvantages, photoresist monomers comprising bisphenol derivatives containing trifluoromethyl and fluorine, and polymers thereof that have low absorbance at the wavelength of 157 nm, and a relatively high glass transition temperature (100~140° C.) are disclosed.

Accordingly, novel photoresist monomers and polymers thereof that can be used for a light source such as ArF (193 nm), VUV (157 nm) and EUV (13 nm) are disclosed.

Photoresist compositions comprising the photoresist polymer described above are also disclosed.

Semiconductor elements produced using the photoresist compositions described above are also disclosed.

DETAILED DESCRIPTION OF THE PRESENTLY PREFERRED EMBODIMENTS

Figure 1:
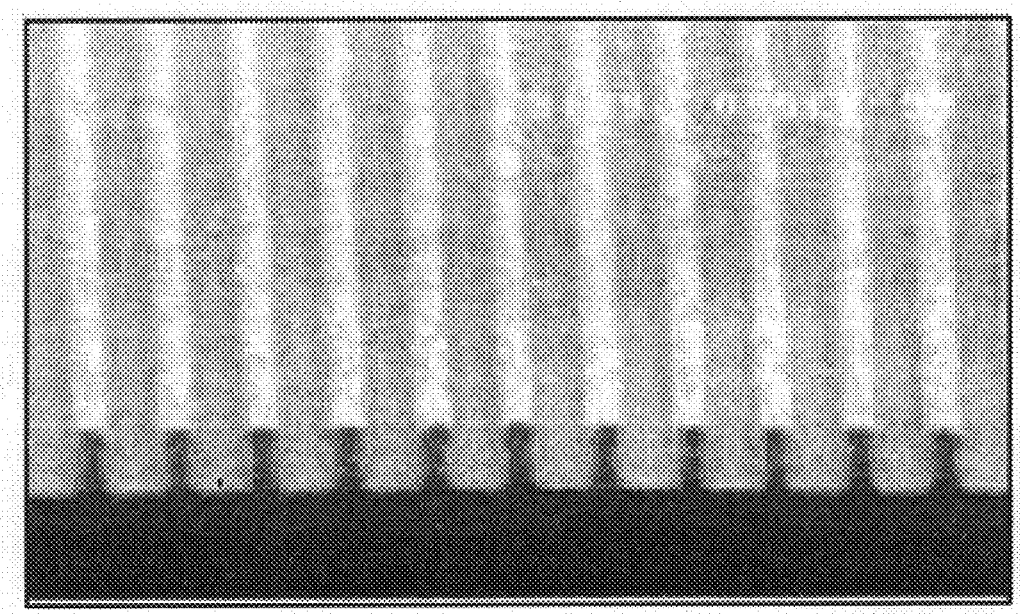
FIGS. 1 to 6 are photographs respectively showing patterns obtained in Examples of the present invention.

The bisphenol derivative according to the present invention is represented by following Formula 1:

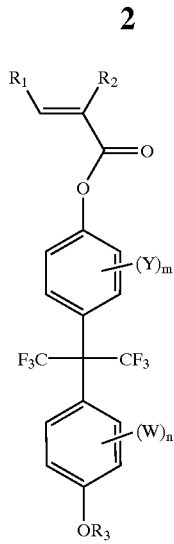

Formula 1 wherein, $R_1$ and $R_2$ individually represent H, substituted or unsubstituted linear or branched ($C_1$–$C_5$) alkyl, or halogen; $R_3$ is an acid labile protecting group; Y and W individually represent H, halogen, $NO_2$, or CN; and m and n denote integers from 0 to 4.

The acid labile protecting group can be any of the known protective groups which prevent the compound from dissolving in an alkaline developing solution. However, under the presence of acid, the acid labile group is substituted with acid, thereby making the compound soluble to the alkaline solution. Some of conventional acid labile protecting groups are disclosed in U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0789 278 (Aug. 13, 1997) and U.S. Pat. No. 6,132,926 (Oct. 17, 2000). Preferred acid labile protecting groups are selected from the group consisting of tetrahydropyran-2-yl, 2-methyl tetrahydropyran-2-yl, tetrahydrofuran-2-yl, 2-methyl tetrahydrofuran-2-yl, 1-methoxypropyl, 1-methoxy-1-methylethyl, 1-ethoxypropyl, 1-ethoxy-1-methylethyl, 1-methoxyethyl, 1-ethoxyethyl, tert-butyl, tert-butoxyethyl, 1-isobutoxyethyl, methylbenzyl and 2-acetylmenth-1-yl.

Preferably, the compound of Formula 1 is selected from the group consisting of compounds of following Formulas 1a to 1f:

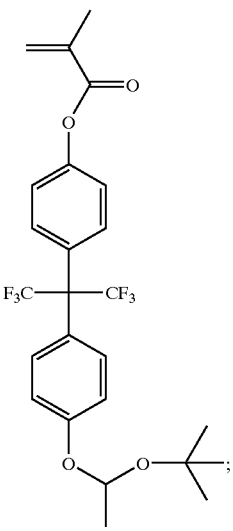

Formula 1a

Formula 1b
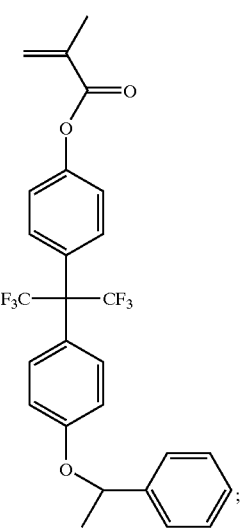
Formula 1c
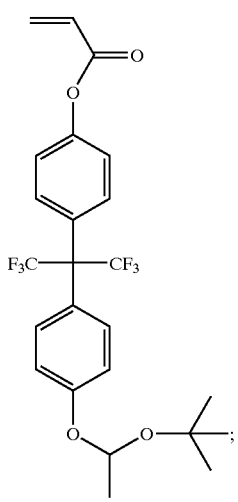
Formula 1d
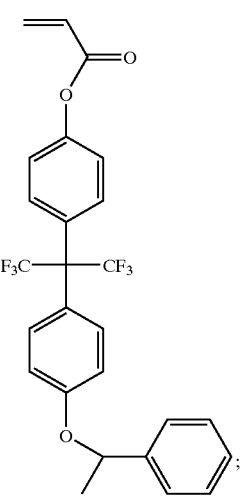
Formula 1e
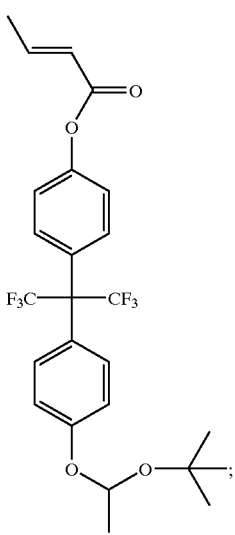
and
Formula 1f
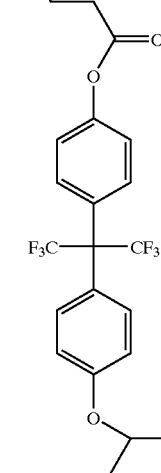
In addition, a photoresist polymer according to the present invention contains the bisphenol derivative of Formula 1.
The photoresist polymer can further contain at least one of the following Formula 2 and Formula 5 as a comonomer:
Formula 2
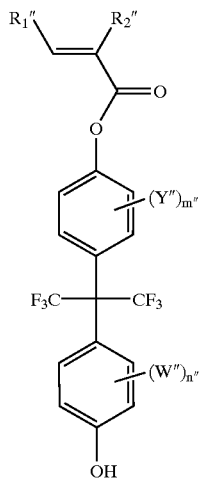

wherein, $R_1''$ and $R_2''$ individually represent H, substituted or unsubstituted linear or branched ($C_1$–$C_5$) alkyl, or halogen; Y" and W" individually represent H, halogen, $NO_2$, or CN; and m" and n" denote integers from 0 to 4.

Formula 5

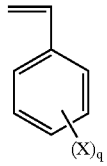

wherein, X represents H, halogen, $NO_2$, or CN; and q denotes an integer from 0 to 4.

Preferably, the compound of Formula 2 is selected from the group consisting of compounds of following Formulas 2a to 2c:

Formula 2a

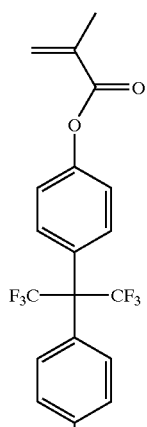

Formula 2b

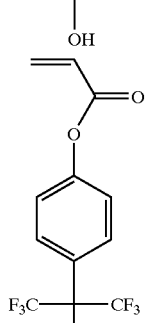

Formula 2c

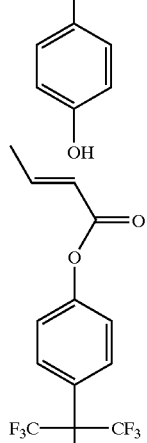

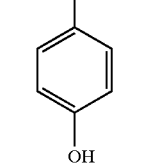

The preferred photoresist polymer according to the present invention have repeating unit represented by following Formula 4:

Formula 4

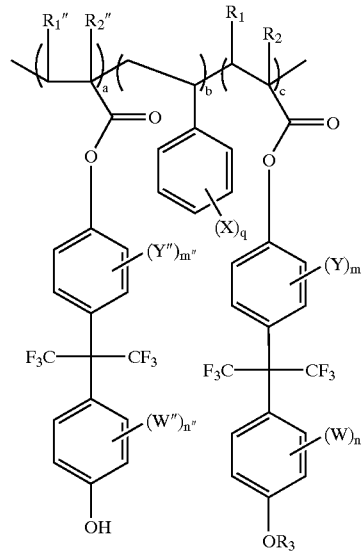

wherein, $R_1$, $R_2$, $R_1''$ and $R_2''$ individually represent H, substitute or unsubstituted linear or branched ($C_1$–$C_5$) alkyl, or halogen; $R_3$ is an acid labile protecting group; X, Y, W, Y" and W" individually represent H, halogen, $NO_2$, or CN; m, n, m", n" and q denote integers from 0 to 4; and a: b: c is 10–90 mol % : 0–50 mol %: 10–60 mol %.

Preferable examples of the repeating unit include compounds of following Formulas 4a to 4h:

Formula 4a

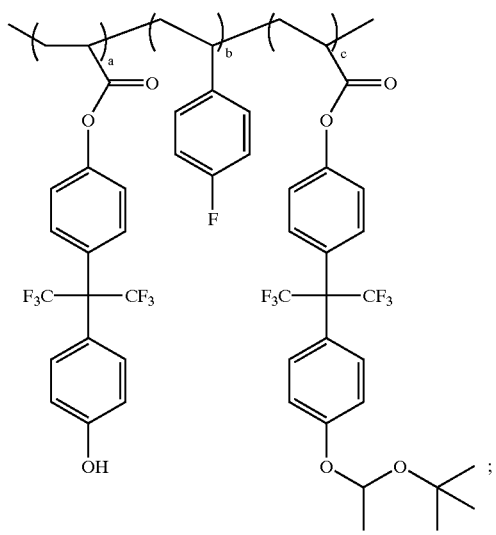

Formula 4b
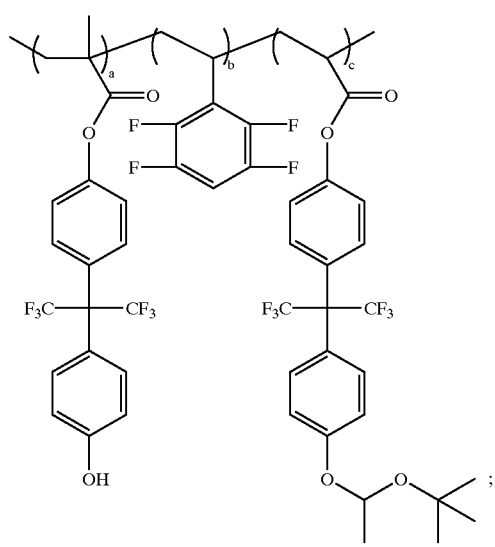
Formula 4c
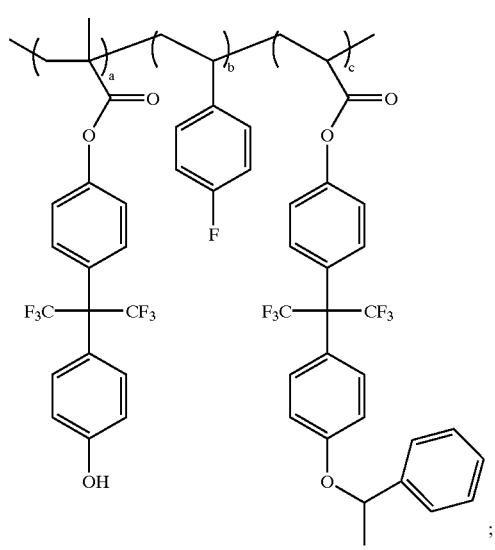
Formula 4d
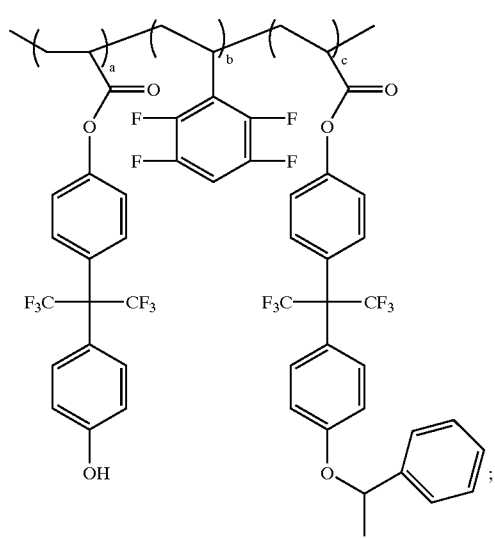
Formula 4e
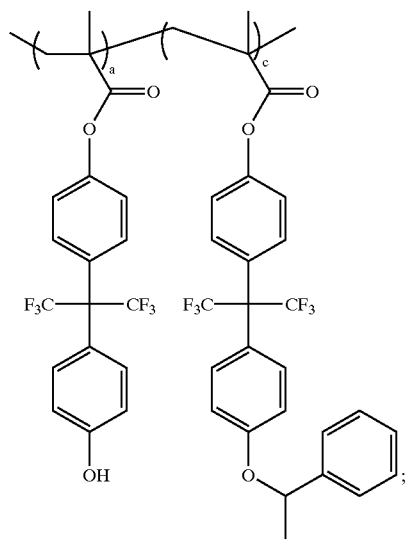
Formula 4f
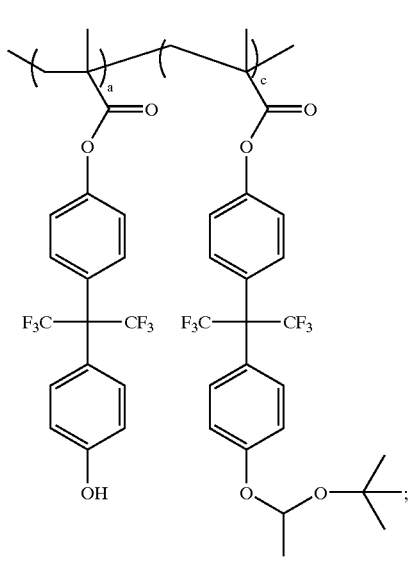
Formula 4g
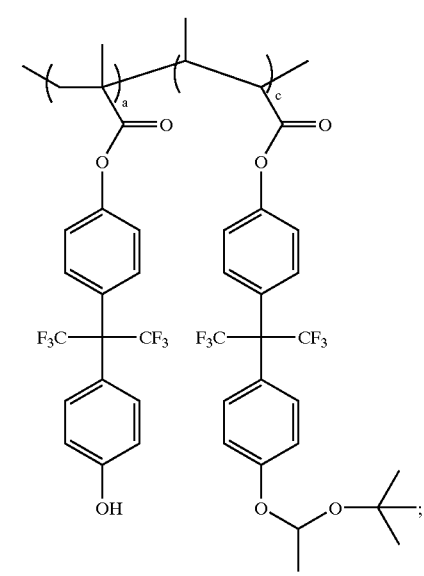
and -continued

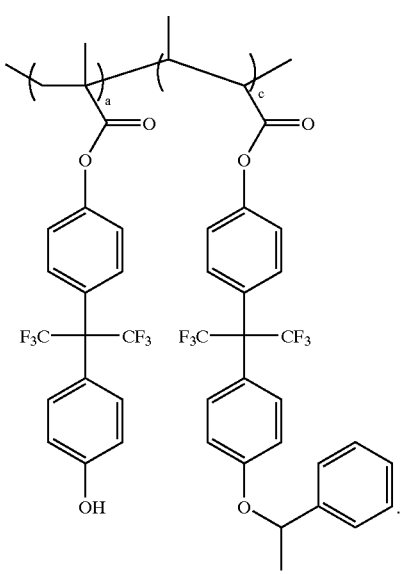

Formula 4h

Polymer of the present invention can be prepared by a various methods. In one particularly preferred method, polymers of the present invention are prepared by the process including the steps of:

(a) admixing (i) a compound of Formula 1, (ii) at least one of the compounds of Formula 2 and Formula 5; and (b) adding a polymerization initiator into the resultant to perform a polymerization.

The step (a) is preferably carried out in a conventional organic solvent, for example, tetrahydrofurane, dimethyl formamide, dimethyl sulfoxide, dioxane, benzene, toluene, xylene and mixture thereof.

The polymerization initiators can be any conventional one, preferably radical polymerization initiator, for example, 2,2'-azobisisobutyronitrile(AIBN), benzoylperoxide, acetylperoxide, laurylperoxide or tert-butylperoxide.

More preferably, after polymerization the polymer is subject to crystallization and/or purification by using diethylether, petroleum ether, alkane, alcohol, water and mixture thereof.

Yet another aspect of the present invention provides a photoresist composition containing (i) a photoresist polymer described above; (ii) an organic solvent; and (iii) a photoacid generator.

Any of conventional photoacid generator, which is able to generate acids when it is exposed to light, can be used. Preferred photoacid generator is sulfide or onium type. Some of conventional photoacid generator are disclosed in U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0789 278 (Aug. 13, 1997) and U.S. Pat. No. 6,132,926 (Oct. 17, 2000). Preferred photoacid generator is diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, triphenylsulfonium hexafluoroarsenate, triphenylsulfonium hexafluoroantimonate, triphenylsulfonium triflate or dibutylnaphthylsulfonium triflate and mixture thereof.

Typically, the amount of photoacid generator used is from about 0.1% by weight to about 10% on the basis of the weight of the photoresist resin employed.

On the other hand, any of conventional organic solvent can be employed for this invention and some of the conventional one are disclosed in U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0789 278 (Aug. 13, 1997) and U.S. Pat. No. 6,132,926 (Oct. 17, 2000). Preferable organic solvents for PR compositions of the present invention is diethylene glycol diethyl ether, methyl 3-methoxypropionate, ethyl 3-ethoxypropionate, propyleneglycol methyl ether acetate, cyclohexanone, 2-heptanone or mixtures thereof.

The amount of solvent used is preferably in the range of from about 400% to about 1500% by weight of the photoresist polymer. This ratio has been found to be particularly useful for obtaining a photoresist layer of a desirable thickness when coated on to a substrate.

A process for forming a photoresist pattern can comprise the steps of:

(a) coating the photoresist composition described above on a substrate to form a photoresist film;

(b) exposing the photoresist film to light ; and (c) developing the photoresist film.

The process for forming the photoresist pattern can further include a soft baking step which is performed before the step (b) and/or a post baking step which is performed after the step (b). Preferably, the soft and post baking steps are performed at the temperature in the range of from about 70 to about 200° C.

Exemplary light sources which are useful for forming the photoresist pattern include ArF, KrF, VUV, EUV, E-beam, X-ray or ion beam. Preferably, the irradiation energy in the step (b) is in the range of between about 1 mJ/cm$^2$ and about 100 mJ/cm$^2$.

Furthermore, a semiconductor device can be manufactured using the photoresist compositions described above.

The disclosed monomers, polymers and compositions will now be described in more details by referring to the examples below, which are not intended to be limiting.

I. Preparation of Photoresist Monomers

EXAMPLE 1

Synthesis of Compound of Formula 2a (HHPPMA)

To 400 ml of anhydrous tetrahydrofuran was added 0.2 mol of hexafluorobisphenol A and 0.2 mol of trimethylamine. The resulting solution was cooled to a temperature of 0° C. A solution obtained by dissolving 0.2 mol of methacryloylchloride in 200 ml of anhydrous tetrahydrofuran was slowly added thereto, and the resulting solution was reacted for 10 hours. Thereafter, the resulting mixture was vacuum-distilled to remove the solvent, and the residual mixture was extracted in aqueous ethyl acetate/0.1 N KOH solution. Aqueous 0.1 IN HCl solution was added to neutralize an organic layer. Then, the organic layer was dehydrated by MgSO$_4$, and filtered, and the solvent was distilled. A product was separated from the thusly-obtained mixture by column chromatography using a mixing solution (ethyl acetate/hexane). The solution containing the product was vacuum-distilled, to prepare 4-[2-(4-hydroxyphenyl)-1,1,1, 3,3,3-hexafluoropropyl]phenyl methacrylate (HHPPMA) of Formula 2a in white solid type (yield: 56%).

EXAMPLE 2

Synthesis of Compound of Formula 2b (HHPPA)

The procedure of Example 1 was repeated but using 0.2 mol of acryloylchloride, instead of using 0.2 mol of methacryloylchloride, to prepare 4-[2-(4-hydroxyphenyl)-1, 1,1,3,3,3-hexafluoropropyl]phenyl acrylate (HHPPA)of Formula 2b in white solid type (yield: 56%).

EXAMPLE 3

Synthesis of Compound of Formula 2c (HHPPC)

The procedure of Example 1 was repeated but using 0.2 mol of crotonylchloride, instead of using 0.2 mol of methacryloylchloride, to prepare 4-[2-(4-hydroxyphenyl)-1,1,1,3,3,3-hexafluoropropyl]phenyl crotonylate (HHPPC) of Formula 2c in white solid type (yield: 56%).

EXAMPLE 4

Synthesis of Compound of Formula 1a (HHPPMA-$^t$-BVE)

To anhydrous tetrahydrofuran was added 0.1 mol of the compound of Formula 2a synthesized in Example 1 and 10 mg of p-toluenesulfonic acid. 0.12 mol of tert-butylvinylether was added thereto, and the resulting solution was reacted for 24 hours at a room temperature. Thereafter, the resulting mixture was vacuum-distilled to remove the solvent, and the residual mixture was extracted in aqueous ethyl acetate/0.1N KOH solution. Aqueous 0.1N HCl solution was added to neutralize an organic layer. Then, the organic layer was dehydrated by $MgSO_4$, and filtered, and the solvent was distilled. A product was separated from the thusly-obtained mixture by column chromatography using a mixing solution(ethyl acetate/hexane). The solution containing the product was vacuum-distilled, to prepare HHPPMA-$^t$-BVE of Formula 1a wherein H of a hydroxyl group of the compound of Formula 2a was substituted with tert-butylvinylether (yield: 91%).

EXAMPLE 5

Synthesis of Compound of Formula 1b (HHPPMA-MB)

To ethanol was added 0.1 mol of the compound of Formula 2a synthesized in Example 1 and 0.1M of KOH. 0.12 mol of (1-bromoethyl)benzene was added thereto, and the resulting solution was reacted at 50° C. for 24 hours. Thereafter, the resulting mixture was vacuum-distilled to remove the solvent, and the residual mixture was extracted in aqueous ethyl acetate/0.1N HCl solution. Then, an organic layer was dehydrated by $MgSO_4$, and filtered, and the solvent was distilled. A product was separated from the thusly-obtained mixture by column chromatography using a mixing solution(ethyl acetate/hexane). The solution containing the product was vacuum-distilled, to prepare HHPPMA-MB of Formula 1b wherein H of a hydroxyl group of the compound of Formula 2a was substituted with methylbenzyl (yield: 91%).

EXAMPLE 6

Synthesis of Compound of Formula 1c (HHPPA-$^t$-BVE)

The procedure of Example 4 was repeated but using 0.1 mol of the compound of Formula 2b synthesized in Example 2, instead of using 0.1 mol of the compound synthesized in Example 1, to prepare HHPPA-$^t$-BVE of Formula 1c wherein H of a hydroxyl group of the compound of Formula 2b was substituted with tert-butylvinylether (yield : 91%).

EXAMPLE 7

Synthesis of Compound of Formula 1d (HHPPA-MB)

The procedure of Example 5 was repeated but using 0.1 mol of the compound of Formula 2b synthesized in Example 2, instead of using 0.1 mol of the compound synthesized in Example 1, to prepare HHPPA-MB of Formula 1d wherein H of a hydroxyl group of the compound of Formula 2b was substituted with methylbenzyl (yield: 91%).

EXAMPLE 8

Synthesis of Compound of Formula 1e (HHPPC-$^t$-BVE)

The procedure of Example 4 was repeated but using 0.1 mol of the compound of Formula 2c synthesized in Example 3, instead of using 0.1 mol of the compound synthesized in Example 1, to prepare HHPPC-$^t$-BVE of Formula 1e wherein H of a hydroxyl group of the compound of Formula 2c was substituted with tert-butylvinylether (yield: 91%).

EXAMPLE 9

Synthesis of Compound of Formula 1f (HHPPC-MB)

The procedure of Example 5 was repeated but using 0.1 mol of the compound of Formula 2c synthesized in Example 3, instead of using 0.1 mol of the compound synthesized in Example 1, to prepare HHPPC-MB of Formula 1f wherein H of a hydroxyl group of the compound of Formula 2c was substituted with methylbenzyl (yield: 91%).

II. Preparation of Photoresist Polymers

EXAMPLE 10

Synthesis of Poly(HHPPMA/4-fluorostyrene/ HHPPMA-$^t$-BVE)

To 80 g of tetrahydrofuran was added 0.1 mol of HAPPMA, 0.02 mol of 4-fluorostyrene, 0.08 mol of HAPPMA-$^t$-BVE and 0.5 g of AIBN. The resulting solution was reacted at 65° C. for 10 hours. Thereafter, tetrahydrofuran was removed by distillation. The polymer was precipitated and filtered in diethylether/petroleum ether, to obtain the polymer of Formula 4a (yield: 65%).

EXAMPLE 11

Synthesis of Poly(HHPPMA/2,3,5,6-tetrafluorostyrene/HHPPA-$^t$-BVE)

To 80 g of tetrahydrofuran was added 0.1 mol of HAPPMA, 0.02 mol of 2,3,5,6-tetrafluorostyrene, 0.08 mol of HAPPA-$^t$-BVE and 0.5 g of AIBN. The resulting solution was reacted at 65° C. for 10 hours. Thereafter, tetrahydrofuran was removed by distillation. The polymer was precipitated and filtered in diethylether/petroleum ether, to prepare the polymer of Formula 4b (yield: 67%).

EXAMPLE 12

Synthesis of Poly(HHPPMA/4-fluorostyrene/ HHPPMA-MB)

To 80 g of tetrahydrofuran was added 0.1 mol of HAPPMA, 0.02 mol of 4-fluorostyrene, 0.08 mol of HAPPMA-MB and 0.5 g of AIBN. The resulting solution was reacted at 65° C. for 10 hours. Thereafter, tetrahydrofuran was removed by distillation. The polymer was precipitated and filtered in diethylether/petroleum ether, to prepare the polymer of Formula 4c (yield: 66%).

EXAMPLE 13

Synthesis of Poly(HHPPA/2,3,5,6-tetrafluorostyrene/HHPPA-MB)

To 80 g of tetrahydrofuran was added 0.1 mol of HAPPA, 0.02 mol of 2,3,5,6-tetrafluorostyrene, 0.08 mol of HAPPA- MB and 0.5 g of AIBN. The resulting solution was reacted at 65° C. for 10 hours. Thereafter, tetrahydrofuran was removed by distillation. The polymer was precipitated and filtered in diethylether/petroleum ether, to prepare the polymer of Formula 4d (yield: 68%).

EXAMPLE 14

Synthesis of Poly(HHPPMA/ HHPPMA-MB)

To 80 g of tetrahydrofuran was added 0.11 mol of HAPPMA, 0.09 mol of HAPPMA-MB and 0.5 g of AIBN. The resulting solution was reacted at 65° C. for 10 hours. Thereafter, tetrahydrofuran was removed by distillation. The polymer was precipitated and filtered in diethylether/petroleum ether, to prepare the polymer of formula 4e (yield: 62%).

EXAMPLE 15

Synthesis of Poly(HHPPMA/HHPPMA-$^t$-BVE)

To 80 g of tetrahydrofuran was added 0.11 mol of HAPPMA, 0.09 mol of HAPPMA-$^t$-BVE and 0.5 g of AIBN. The resulting solution was reacted at 65° C. for 10 hours. Thereafter, tetrahydrofuran was removed by distillation. The polymer was precipitated and filtered in diethylether/petroleum ether, to prepare the polymer of 4f (yield: 61%).

EXAMPLE 16

Synthesis of Poly(HHPPMA/HHPPC-$^t$-BVE)

To 80 g of tetrahydrofuran was added 0.11 mol of HAPPMA, 0.09 mol of HAPPC-$^t$-BVE and 0.5 g of AIBN. The resulting solution was reacted at 65° C. for 10 hours. Thereafter, tetrahydrofuran was removed by distillation. The polymer was precipitated and filtered in diethylether/petroleum ether, to prepare the polymer of 4 g (yield: 62%).

EXAMPLE 17

Synthesis of Poly(HHPPMA/HHPPC-MB)

To 80 g of tetrahydrofuran was added 0.11 mol of HAPPMA, 0.09 mol of HAPPC-MB and 0.5 g of AIBN. The resulting solution was reacted at 65° C. for 10 hours. Thereafter, tetrahydrofuran was removed by distillation. The polymer was precipitated and filtered in diethylether/petroleum ether, to prepare the polymer of 4h (yield: 64%).

III. Preparation of Photoresist Compositions and Formation of Patterns

EXAMPLE 18

To 40 g of diethylene glycol diethylether was added 2 g of the polymer prepared in Example 10 and 0.024 g of triphenylsulfonium triflate. The resulting solution was filtered through 0.20 μm filter to obtain a photoresist composition.

The photoresist composition thus prepared was spin-coated on a silicon wafer and soft-baked at 110° C. for 90 seconds. After baking, the photoresist was exposed to light using a KrF laser exposer, and then post-baked at 110° C. for 90 seconds. When the post-baking was completed, it was developed in 2.38 wt % aqueous TMAH solution for 40 seconds, to obtain 0.13 μm L/S pattern (see FIG. 1).

EXAMPLE 19

Figure 2:
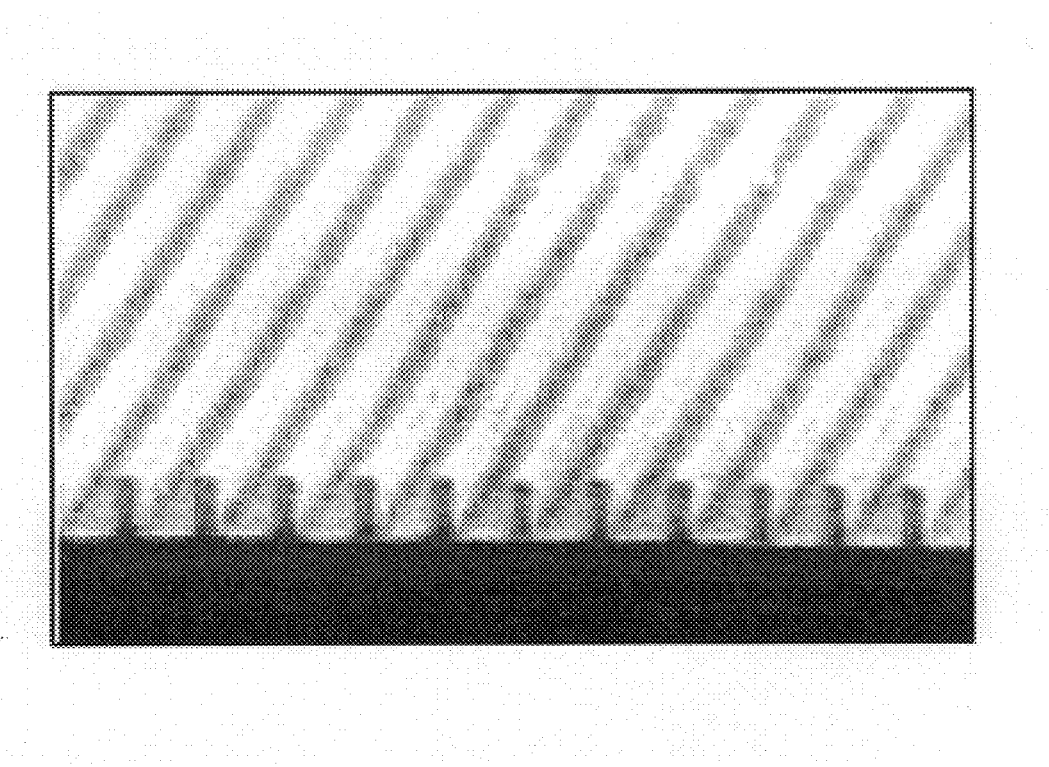

The procedure of Example 18 was repeated but using the polymer prepared in Example 11, instead of using the polymer prepared in Example 10, to obtain 0.13 μm L/S pattern (see FIG. 2).

EXAMPLE 20

Figure 3:
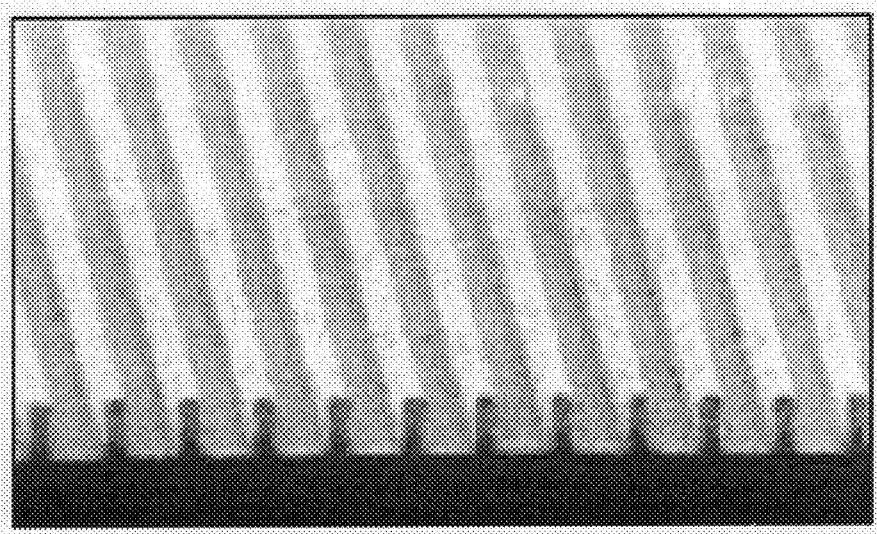

The procedure of Example 18 was repeated but using the polymer prepared in Example 12, instead of using the polymer prepared in Example 10, to obtain 0.13 μm L/S pattern (see FIG. 3).

EXAMPLE 21

Figure 4:
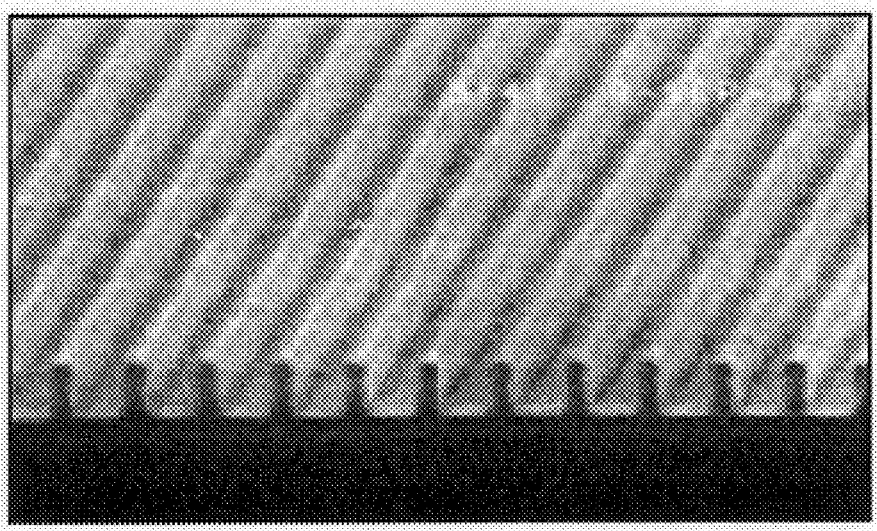

The procedure of Example 18 was repeated but using the polymer prepared in Example 13, instead of using the polymer prepared in Example 10, to obtain 0.13 μm L/S pattern (see FIG. 4).

EXAMPLE 22

Figure 5:
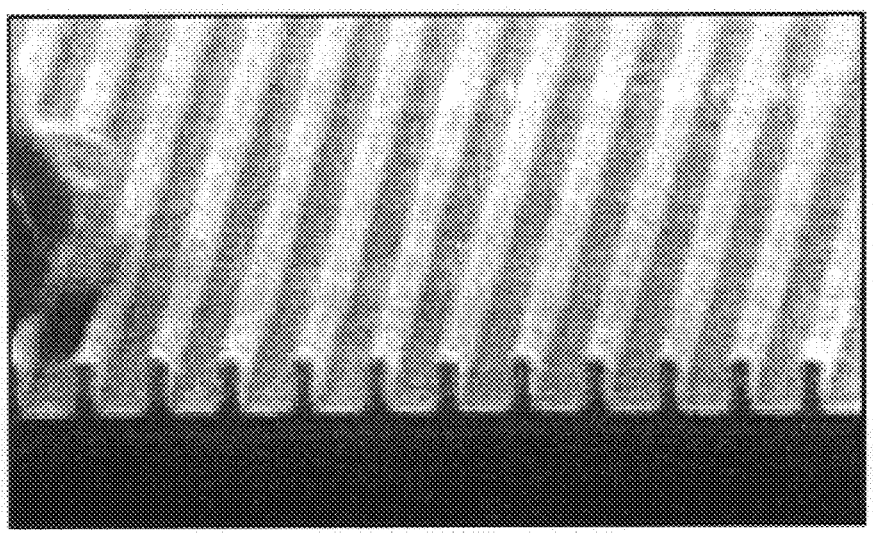

The procedure of Example 18 was repeated but using the polymer prepared in Example 14, instead of using the polymer prepared in Example 10, to obtain 0.13 μm L/S pattern (see FIG. 5).

EXAMPLE 23

Figure 6:
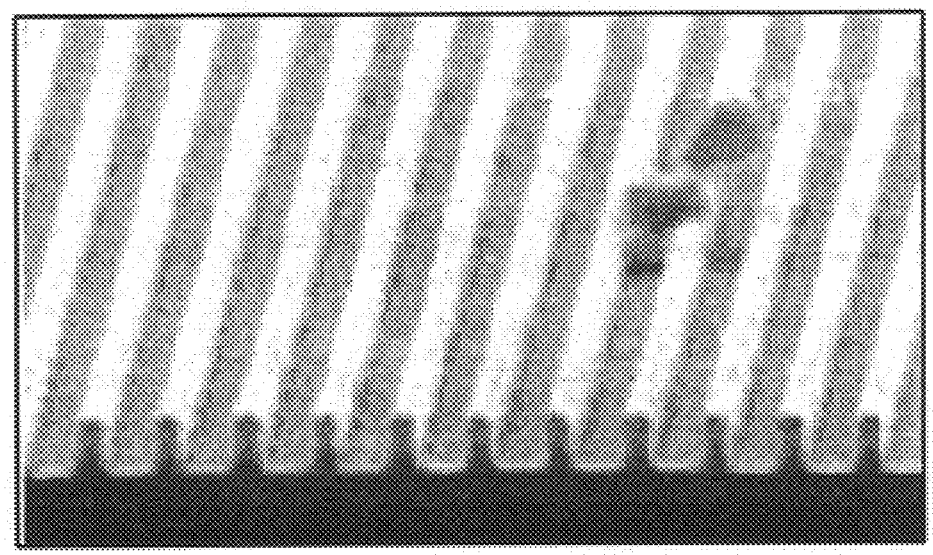

The procedure of Example 18 was repeated but using the polymer prepared in Example 15, instead of using the polymer prepared in Example 10, to obtain 0.13 μm L/S pattern (see FIG. 6).

EXAMPLE 24

The procedure of Example 18 was repeated but using the polymer prepared in Example 16, instead of using the polymer prepared in Example 10, to obtain 0.13 μm L/S pattern.

EXAMPLE 25

The procedure of Example 18 was repeated but using the polymer prepared in Example 17, instead of using the polymer prepared in Example 10, to obtain 0.13 μm L/S pattern.

As discussed earlier, a photoresist pattern having excellent durability, etching resistance, reproducibility and resolution can be formed by employing the photoresist compositions of the present invention. In addition, the photoresist compositions can be used to form an ultrafine pattern of DRAM over 4G and 16G as well as DRAM below 1G Moreover, the photoresist polymer comprising fluorine has high light transmittance at a low wavelength light source, and thus is suitable for VUV, EUV and E-beam.

What is claimed:

1. A bisphenol derivative, used for a photoresist monomer, represented by following Formula 1:

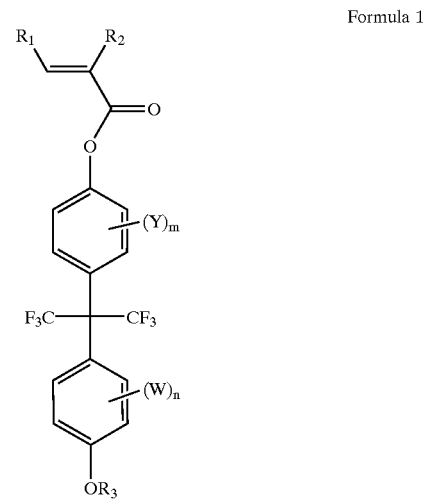

Formula 1 wherein, $R_1$ and $R_2$ individually are selected from the group consisting of H, $(C_1-C_5)$ alkyl, and halogen;

$R_3$ is an acid labile protecting group;

Y and W individually are selected from the group consisting of H, halogen, $NO_2$, and CN; and m and n denote integers ranging from 0 to 4.

2. The bisphenol derivative according to claim 1, wherein the compound of Formula 1 is selected from the group consisting of compounds of following Formulas 1a to 1f:

Formula 1a

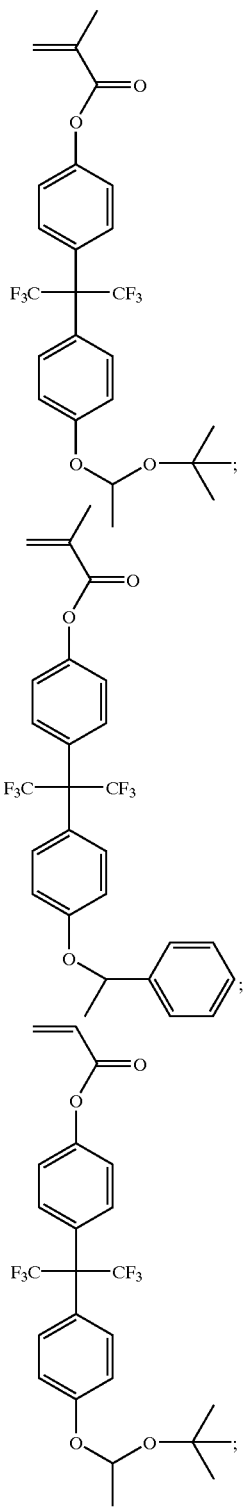

Formula 1b

Formula 1c

Formula 1d

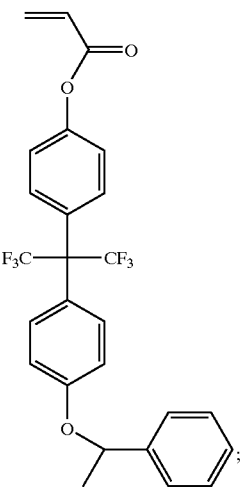

Formula 1e

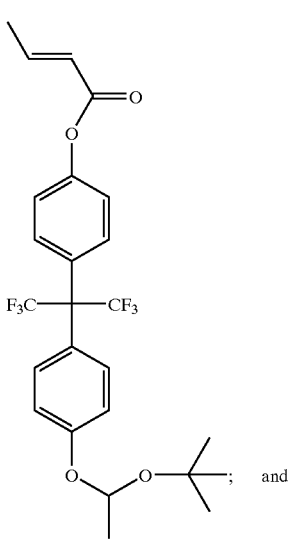

and

Formula 1f

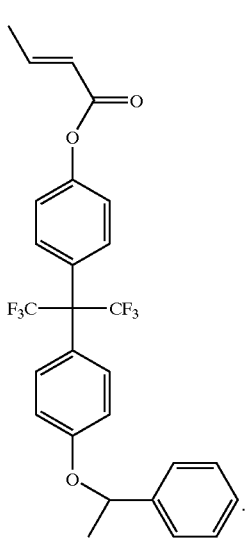

3. The bisphenol derivative according to claim 1, wherein the acid labile protecting group is selected from the group consisting of tetrahydropyran-2-yl, 2-methyl tetrahydropyran-2-yl, tetrahydrofuran-2-yl, 2-methyl tetrahydrofuran-2-yl, 1-methoxypropyl, 1-methoxy-1-methylethyl, 1-ethoxypropyl, 1-ethoxy-1-methylethyl, 1-methoxyethyl, 1-ethoxyethyl, tert-butyl, tert-butoxyethyl, 1-isobutoxyethyl, methylbenzyl and 2-acetylmenth-1-yl.

4. A photoresist polymer comprising the bisphenol derivative of claim 1.

5. The photoresist polymer according to claim 4, further comprising at least one of the compound of following Formula 2 and Formula 5 as a comonomer:

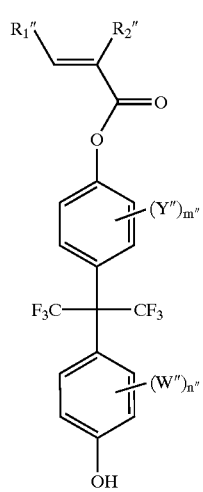

Formula 2 wherein, $R_1''$ and $R_2''$ individually are selected from the group consisting of H, ($C_1$–$C_5$) alkyl, and halogen;

Y" and W" individually are selected from the group consisting of H, halogen, $NO_2$, and CN; and m" and n" denote integers ranging from 0 to 4;

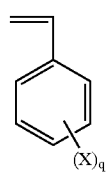

Formula 5 wherein, X represents H, halogen, $NO_2$, or CN; and q denotes an integer from 0 to 4.

6. The photoresist polymer according to claim 5, wherein the compound of Formula 2 is selected from the group consisting of compounds of the following Formulas 2a to 2c:

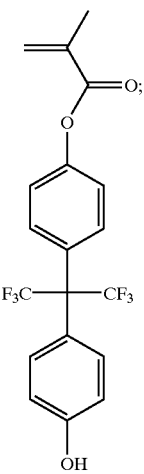

Formula 2a

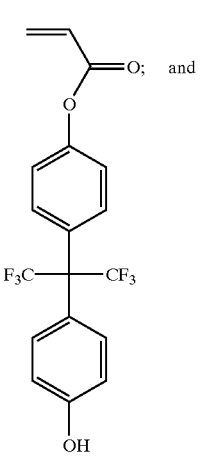

Formula 2b and

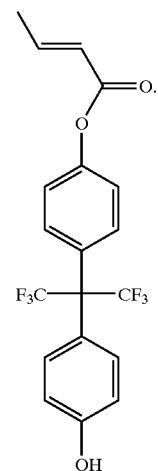

Formula 2c

7. The photoresist polymer according to claim 4, comprising repeating unit of the following Formula 4:

Formula 4

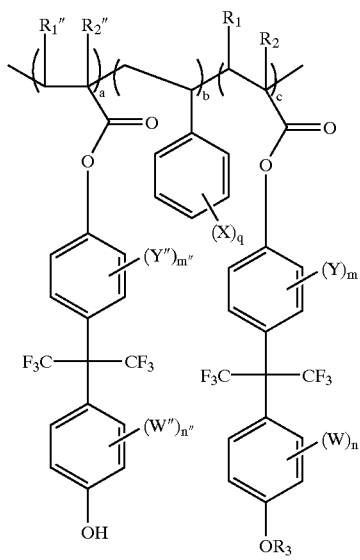

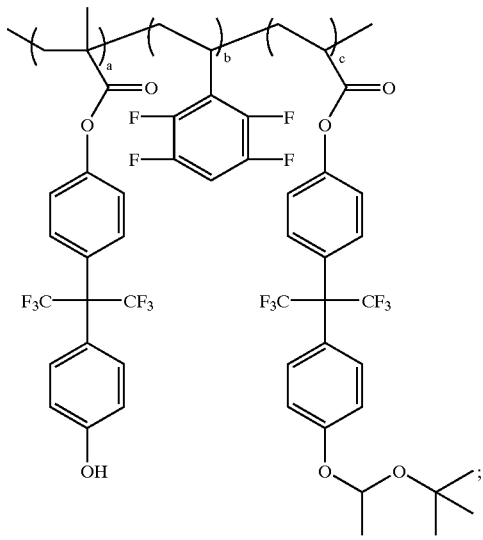

Formula 4b wherein, $R_1$, $R_2$, $R_1''$ and $R_2''$ individually are selected from the group consisting of H, ($C_1$–$C_5$) alkyl, and halogen;

$R_3$ is an acid labile protecting group;

X, Y, W, Y" and W" individually are selected from the group consisting of H, halogen, $NO_2$, and CN;

m, n, m", n" and q denote integers ranging from 0 to 4; and a:b:c is 10–90 mol %: 0–50 mol %: 10–60 mol %.

8. The photoresist polymer according to claim 7, wherein the repeating unit is selected from the group consisting of compounds of the following Formulas 4a to 4h:

Formula 4c

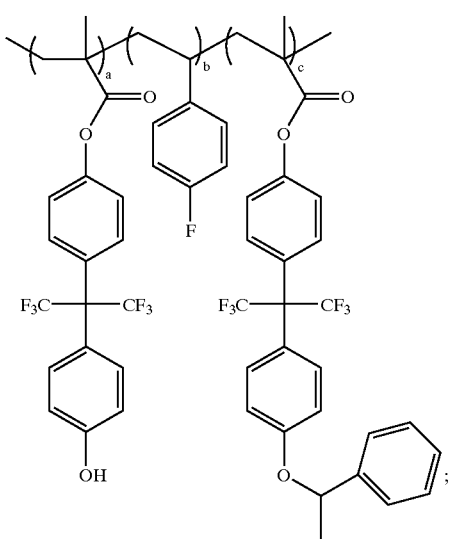

Formula 4a

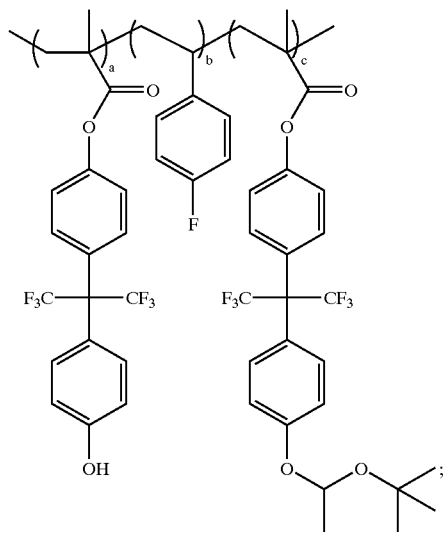

Formula 4d

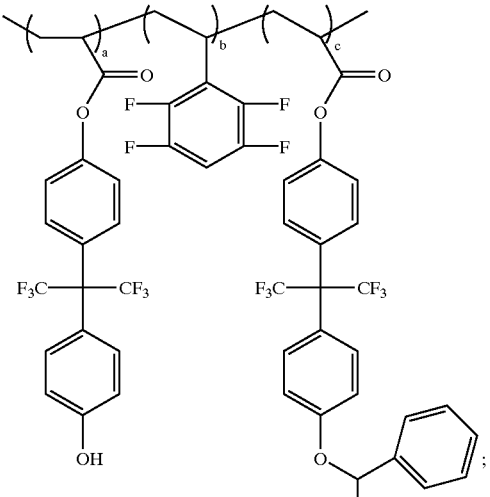

Formula 4e

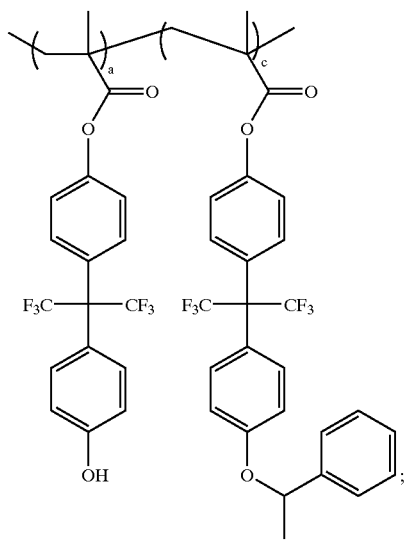

Formula 4f

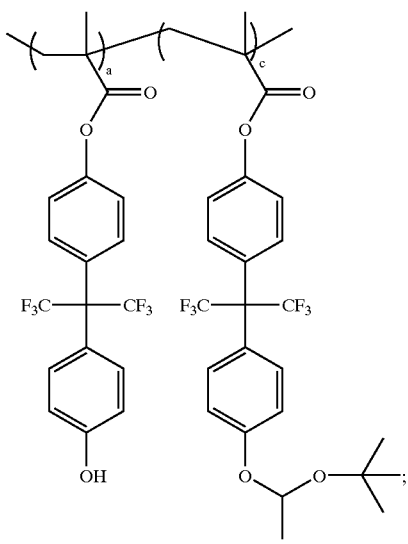

Formula 4g

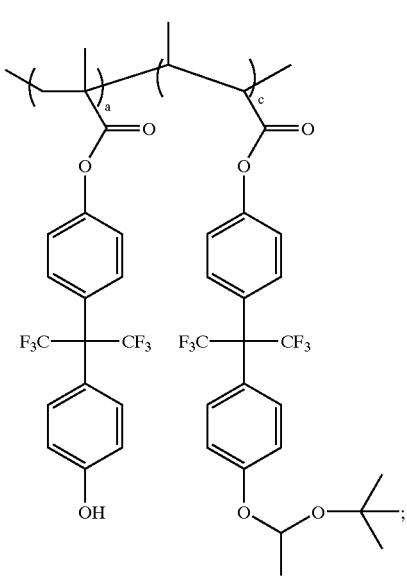
and

Formula 4h

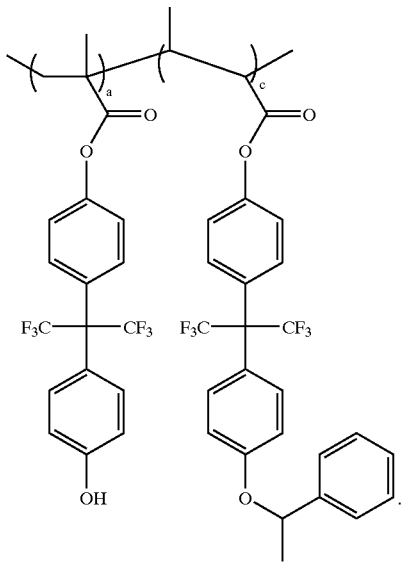

9. A process for preparing a repeating unit of a photoresist polymer of claim 7, comprising the steps of:
   (a) admixng (i) a compound of the following Formula 1 and (ii) at least one of the compound of the following Formula 2 and Formula 5; and
   (b) adding a polymerization initiator into the resultant to perform a polymerization:

Formula 1

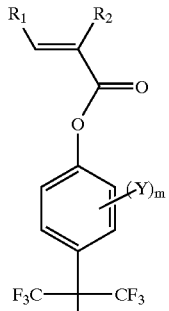

Formula 2

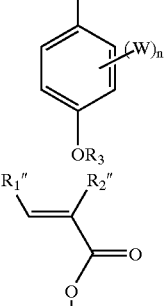

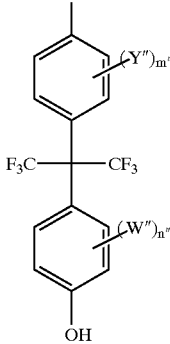

Formula 5

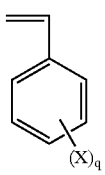

wherein, $R_1$, $R_2$, $R_1''$ and $R_2''$ individually are selected from the group consisting of H, ($C_1$–$C_5$) alkyl, and halogen;

$R_3$ is an acid labile protecting group;

X, Y, W, Y" and W" individually are selected from the group consisting of H, halogen, $NO_2$, and CN; and m, n, m", n", n" and q denote integers ranging from 0 to 4.

10. The process according to claim 9, wherein the step (a) is carried out in a polymerization solvent selected from the group consisting of tetrahydrofurane, dimethylformamide, dimethylsulfoxide, dioxane, benzene, toluene, xylene and mixtures thereof.

11. The process according to claim 9, wherein the polymerization initiator is selected from the group consisting of 2,2'-azobisisobutyronitrile(AIBN), benzoylperoxide, acetylperoxide, laurylperoxide and tert-butylperoxide.

12. A photoresist composition comprising:
(i) the photoresist polymer of claim 4;
(ii) an organic solvent; and
(iii) a photoacid generator.

13. The photoresist composition according to claim 12, wherein the photoacid generator is selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, triphenylsulfonium hexafluoroarsenate, triphenylsulfonium hexafluoroantimonate, triphenylsulfonium triflate, dibutylnaphthylsulfonium triflate and mixtures thereof.

14. The photoresist composition according to claim 12, wherein the organic solvent is selected from the group consisting of diethylene glycol diethyl ether, methyl 3-methoxypropionate, ethyl 3-ethoxypropionate, propylene glycol methyl ether acetate, cyclohexanone, 2-heptanone and mixtures thereof.

15. A process for forming a photoresist pattern, comprising the steps of:
(a) coating the photoresist composition of claim 12 on a substrate to form a photoresist film;
(b) exposing the photoresist film to light; and
(c) developing the photoresist film.

16. The process according to claim 15, further comprising a soft baking step before step (b) and/or a post baking step after step (b).

17. The process according to claim 16, wherein the soft and post baking steps are performed at the temperature ranging from 70 to 200° C.

18. The process according to claim 15, wherein the source of the light is selected from the group consisting of ArF, KrF, EUV, VUV, E-beam, X-ray and ion beam.

19. The process according to claim 15, wherein the irradiation energy is in the range of from 1 $mJ/cm^2$ to 100 $mJ/cm^2$.

20. A semiconductor element manufactured according to the process of claim 15.

* * * * *

UNITED STATES PATENT AND TRADEMARK OFFICE
CERTIFICATE OF CORRECTION

PATENT NO.   : 6,627,383 B2
DATED        : September 30, 2003
INVENTOR(S)  : Geun-Su Lee et al.

It is certified that error appears in the above-identified patent and that said Letters Patent is hereby corrected as shown below:

Title page,
Item [75], Inventors, please delete "Geun Su Lee, Ichon-shi (KR); Jae Chang Jung, Ichon-shi (KE); Min Ho Jung, Ichon-shi (KR); Ki Ho Baik, Ichon-shi (KR)" and replace with -- Geun Su Lee, Kyoungki-do (KR); Jae Chang Jung, Kyoungki-do (KR); Min Ho Jung, Kyoungki-do (KR); Ki Ho Baik, Kyoundki-do (KR) --.

Column 15,
Lines 10-65, please delete the formulas and replace it with the following formulas:

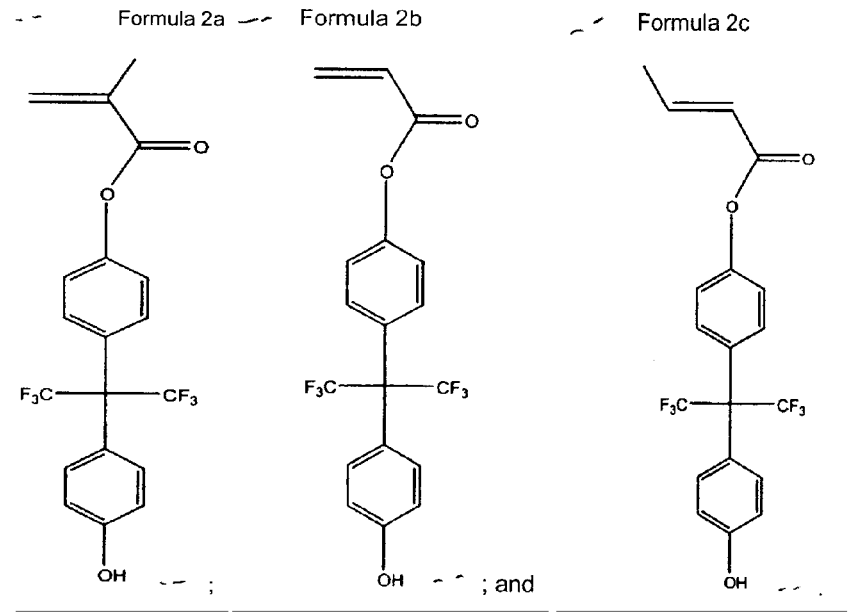

UNITED STATES PATENT AND TRADEMARK OFFICE
CERTIFICATE OF CORRECTION

PATENT NO. : 6,627,383 B2
DATED : September 30, 2003
INVENTOR(S) : Geun-Su Lee et al.

It is certified that error appears in the above-identified patent and that said Letters Patent is hereby corrected as shown below:

Column 22,
Line 25, please delete the word "of." and replace it with -- of --.
Line 26, please delete the word "admixng" and replace it with -- admixing --.

Signed and Sealed this

Twenty-third Day of March, 2004

JON W. DUDAS
*Acting Director of the United States Patent and Trademark Office*